United States Patent [19]

Shibata et al.

[11] Patent Number: 4,831,143

[45] Date of Patent: May 16, 1989

[54] PYRIMIDINE COMPOUND

[75] Inventors: Toshihiro Shibata; Masaki Kimura, both of Saitama; Norio Kurosawa, Tokyo, all of Japan

[73] Assignee: Adeka Argus Chemical Co., Ltd., Tokyo, Japan

[21] Appl. No.: 136,649

[22] Filed: Dec. 22, 1987

[30] Foreign Application Priority Data

Dec. 26, 1986 [JP] Japan .................. 61-314699

[51] Int. Cl.$^4$ .................. G02F 1/13; C09K 19/34; C07D 239/02
[52] U.S. Cl. .................. 544/335; 252/299.01; 252/299.61; 350/350 R; 350/350 S
[58] Field of Search .......... 252/299.01, 299.5, 299.61; 250/250 S, 250 R; 544/335

[56] References Cited

U.S. PATENT DOCUMENTS 4,725,688  2/1988  Taguchi et al. .................. 252/299.61

FOREIGN PATENT DOCUMENTS 3515373  11/1986  Fed. Rep. of Germany .................. 252/299.61
61-271279  12/1986  Japan .................. 252/299.61

Primary Examiner—Teddy S. Gron
Attorney, Agent, or Firm—Young & Thompson

[57] ABSTRACT

The present invention discloses an optically active pyrimidine compound represented by the following general formula:

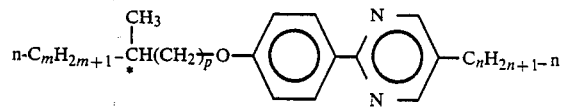

wherein
  m is 3 to 14
  n is 4 to 18; p is 3 to 5; and
  *C represents an asymmetric carbon atom.

The pyrimidine compound of the present invention is a liquid crystal compound useful as an electrooptic element wherein the response of the ferroelectric liquid crystal to an electric field is utilized.

5 Claims, No Drawings

PYRIMIDINE COMPOUND

BACKGROUND OF THE INVENTION

1. Field of the Invention:

This invention relates to an optically active pyrimidine compound which is a liquid crystal compound useful as an electrooptic element wherein the response of the ferroelectric smectic liquid crystal to an electric field is utilized.

2. Description of the Prior Art:

Liquid crystals have been employed as various electrooptic elements such as a display device of a watch or an electronic calculator. Most of liquid crystal display devices which have been put into practical use hitherto are those wherein the dielectric orientation effect of a nematic or cholesteric liquid crystal is utilized. However the application of these liquid crystals to a display device involving a large number of pixels is accompanied by some troubles such as a low response, poor contrast caused by the lack of drive margin and unsatisfactory visual angles. Therefore there has been frequently attempted to develop a MOS or TFT panel involving formation of a switching device for each pixel.

U.S. Pat. No. 4,367,924 has disclosed a liquid crystal device wherein a smectic phase based on a novel displaying principle is used to thereby overcome the disadvantages as described above.

Further it has been known that a liquid crystal compound exhibiting a C* or H phase consisting of optically active molecules generally has an electrical dipole density P and is ferroelectric. Such a chiral smectic liquid crystal having electrical dipoles is more strongly affected by an electric field than dielectric anisotropic ones. As a result, the polarity of P is made parallel to the direction of the electric field. Thus the direction of the molecules can be controlled by reversing the direction of the applied electric field. Then the average change in the direction of the major axes of these molecules is detected with the use of two polarizing plates. Thus the liquid crystal can be used as an electrooptic element.

The effect of the spontaneous polarization of this electrooptic element, wherein the response of the smectic C* or H phase to an electric field is utilized, and the electric field exert an action 10 3 to 10 4 times as high as those of dielectric anisotropic ones. Thus the former shows a high-speed response compared with a TN liquid crystal device. Further it is possible to impart thereto a memory function by appropriately controlling the orientation. Therefore it is expected to apply the same to a high-speed optical shutter or to a display of a large capacity.

There have been synthesized various chiral smectic liquid crystal compounds having a ferroelectricity and the properties thereof have been studied.

For example, an optically active 2-(4-alkoxyphenyl)-5-alkylpyrimidine compound has been proposed as a compound which is stable to water and shows a chiral smectic phase within a wide range of temperature in Japanese Patent Laid-Open No.93170/1986.

However each compound as described above is available only within a restricted range of temperature. Namely, its insufficient properties, in particular, at a low temperature make it unsatisfactory from the practical viewpoint.

SUMMARY OF THE INVENTION

It is the main object of the present invention to provide a compound useful as a liquid crystal which is suitable for preparing a composition available over an unlimited temperature range and, in particular, having a liquid crystal temperature lower than room temperature.

We have attempted to develop a pyrimidine liquid crystal compound which shows a chiral smectic phase over a wider temperature range. As a result, we have found that an optically active pyrimidine compound of the following general formula (I), wherein an alkyl group having a longer chain that an ethyl group does is bonded to the asymmetric carbon atom, shows a chiral smectic phase over a wide range of temperature involving, in particular, a low temperature region, thus completing the present invention.

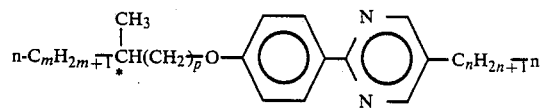

wherein
m is 3 to 14
n is 4 to 18 ; p is 3 to 5 ; and
*C represents an asymmetric carbon atom.

DETAILED DESCRIPTION OF THE INVENTION

The compound of the present invention as represented by the above general formula can be prepared by a common method used in synthesizing phenylpyrimidine compounds.

For example, it may be prepared by etherifying 5-alkyl-2-(4-hydroxyphenyl) pyrimidine with the corresponding optically active alcohol ; or by etherifying 4-cyanophenol with the corresponding optically active alcohol and converting the resulting product into pyrimidine in a conventional manner.

A 5-alkyl-2-(4-hydroxyphenyl) pyrimidine compound may be prepared by a conventional method comprising, for example, converting 4-cyanophenol into a benzyl ether in a conventional manner, converting the resulting ether into 4-benzyloxy-benzamidine hydrochloride, reacting the obtained product with an n-alkylmalonic acid diester to give a 2-(4-benzyloxyphenyl)-4,6-dihydroxy-5-n-alkyl-pyrimidine and then chlorinating and reducing the product.

The obtained compound of the present invention as represented by the above general formula can be used alone as a liquid crystal material. Alternately it can be mixed with other liquid crystal compound(s).

To further illustrate the present invention, the following Examples will be given.

Example 1 : Synthesis of 2-(4-(4-methyloctoxy)-phenyl)-5-n-decylpyrimidine 0.38 g of 55% sodium hydride and 10 ml of dimethylformamide were weighed out and a solution of 2 g of 2-(4-hydroxyphenyl)-5-n-decylpyrimidine in 3 ml of dimethylformamide was added dropwise thereto under ice cooling. After the completion of the addition, the resulting mixture was stirred at room temperature for one hour. Then p-toluene-sulfonate of optically active 4-methyloctanol was added dropwise thereto and the resulting mixture was stirred at 90° C. for two hours. After cooling, the reaction mixture was poured into ice/water, extractd with diethyl ether and dried followed by removal of the solvent. The residue was purified on a silica gel column to thereby give 1.5 g of optically active 2-(4-(4-methyloctoxy)phenyl)-5-n-decylpyrimidine.

Infrared spectroscopy (cm$^{-1}$):
2900(s), 2850(m), 1605(w), 1580(m), 1460(m), 1430(m), 1250(m) and 8000(m)
H-NMR (ppm)
8.30(s) 2H, 8.20(d), J=9Hz 2H,
6.72(d), J=9Hz 2H, 3.85(t), J=6Hz 2H,
2.45(t), J=7Hz 2H This compound was poured into a transparent glass electrode cell of 2 μm in thickness, which had been subjected to orientation by rubbing, and heated to 90° C. to thereby give an isotropic liquid.

The liquid crystal cell thus obtained was cooled under a crossed Nicol prism while applying rectangular pulses (15 V, 1 Hz) thereto. As a result, definite switching behaviors were observed within a temperature range of 50.5° C. to 4° C.

Further the following phase transition was observed under a polarization microscope:

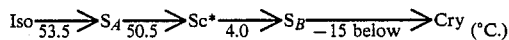

It has been confirmed that the above compound of the present invention shows an Sc* phase over a wide temperature range, i.e., over 45° C. involving a temperature as low as 4° C., and that it shows an $S_B$ phase under the Sc* phase and maintains the smectic domain state even at a temperature of −15° C. or below, which obviously suggests that it is suitable for the preparation of a composition showing a low liquid crystal temperature.

In contrast thereto, the compound as described in Japanese Patent Laid-Open No. 93170/1986, wherein an ethyl group is employed as the alkyl group bonded to the asymmetric carbon atom, shows an Sc* phase at a temperature exceeding approximately 15° C. Thus the physical properties thereof at a low temperature are unsatisfactory.

Example 2: Synthesis of 2-(4-(4-methyloctoxy)phenyl)-5-n-octylpyrimidine

The procedure of Example 1 was followed except that the 2-(4-hydroxyphenyl)-5-n-decylpyrimidine was replaced by 2-(4-hydroxyphenyl)-5-n-octylpyrimidine to thereby give the title compound.

Infrared spectroscopy (cm$^{-1}$):
2900(s), 2840(m), 1600(w), 1580(m), 1455(m), 1420(m), 1240(m) and 800(m)
H-NMR (ppm)
8.27(s) 2H, 8.18(d), J=9Hz 2H,
6.70(d), J=9Hz 2H, 3.85(t), J=6Hz 2H,
2.47(t), J=7Hz 2H This compound was poured into a transparent glass electrode cell of 2 μm in thickness, which had been subjected to orientation by rubbing, and heated to 90° C. to thereby give an isotropic liquid.

The liquid crystal cell thus obtained was cooled under a crossed Nicol prism while applying rectangular pulses (15 V, 1 Hz) thereto. As a result, definite switching behaviors were observed within a temperature range of 19.5° C. to 11.5° C.

Further the following phase transition was observed under a polarization microscope:

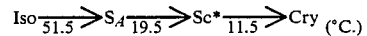

It is obvious that the above compound of the present invention, which shows an Sc* phase at a temperature lower than room temperature, is useful as a liquid crystal compound or as a blending agent for the preparation of a composition showing a liquid crystal temperature lower than room temperature.

Example 3: Synthesis of 2-(4-(4-methyldodecyloxy)phenyl)-5-n-octylpyrimidine

The procedure of Example 2 was followed except that the 4-methyloctanol was replaced by 4-methyldodecanol to thereby give the title compound.

Infrared spectroscopy (cm$^{-1}$):
2900(s), 2850(s), 1600(w), 1580(m), 1455(m), 1420(m), 1245(m) and 795(m)
H-NMR (ppm)
8.32(s) 2H, 8.12(d), J=9Hz 2H,
6.73(d), J=9Hz 2H, 3.88(t), J=6Hz 2H,
2.49(t), J=7Hz 2H Further the following phase transition was observed under a polarization microscope:

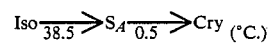

Example 4: Synthesis of 2-(4-(6-methyldecyloxy)phenyl)-5-n-octylpyrimidine

The procedure of Example 1 was followed except that the 4-methyloctanol was replaced with 6-methyldecanol to thereby give the title compound.

Infrared spectroscopy (cm$^{-1}$):
2900(s), 2850(m), 1600(w), 1580(m), 1455(m), 1425(m), 1245(m) and 795(m)
H-NMR (ppm)
8.28(s) 2H, 8.20(d), J=9Hz 2H,
6.70(d), J=9Hz 2H, 3.85(t), J=6Hz 2H,
2.47(t), J=7Hz 2H This compound was poured into a transparent glass electrode cell of 2 μm in thickness, which had been subjected to orientation by rubbing, and heated to 90° C. to thereby give an isotropic liquid.

The liquid crystal cell thus obtained was cooled under a crossed Nicol prism while applying rectangular pulses (15 V, 1 Hz) thereto. As a result, definite switching behaviors were observed within a temperature range of 31° C. to 7.5° C.

Further the following phase transition was observed under a polarization microscope:

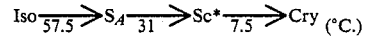

It is obvious that the above compound of the present invention, which shows an Sc* phase at a temperature lower than room temperature, is useful as a liquid crystal compound or as a blending agent for the preparation of a composition showing a liquid crystal temperature lower than room temperature.

Thus the compound of the present invention is useful as a liquid crystal compound suitable for the preparation of a composition having a liquid crystal temperature lower than room temperature and as a blending agent suitable for the preparation of a composition having a liquid crystal temperature lower than room temperature.

What is claimed is:

1. An optically active pyrimidine compound represented by the following general formula:

Formula (I)

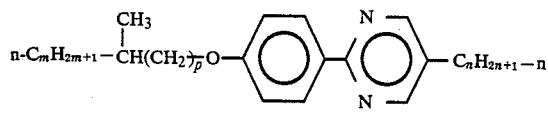

wherein
m is 3 to 14;
n is 4 to 18; p is 3 to 5; and
*C represents an asymmetric carbon atom.

2. A pyrimidine compound as set forth in claim 1, which is 2-(4-(4-methyloctoxy)-phenyl)-5-n-decyl-pyrimidine.

3. A pyrimidine compound as set forth in claim 1, which is 2-(4-(4-methyloctoxy)-phenyl)-5-n-octyl-pyrimidine.

4. A pyrimidine compound as set forth in claim 1, which is 2-(4-(4-methyldodecyloxy)-phenyl)-5-n-octyl-pyrimidine.

5. A pyrimidine compound as set forth in claim 1, which is 2-(4-(6-methyldecyloxy)-phenyl)-5-n-octyl-pyrimidine.

* * * * *